United States Patent [19]

Newton

[11] 4,453,935

[45] Jun. 12, 1984

[54] DISPOSABLE CONTAINER-APPLICATOR WITH LEAK-PROOF COVER

[75] Inventor: W. Howard Newton, Cincinnati, Ohio

[73] Assignee: Chester Labs, Inc., Erlanger, Ky.

[21] Appl. No.: 558,569

[22] Filed: Dec. 6, 1983

Related U.S. Application Data

[63] Continuation of Ser. No. 369,092, Apr. 16, 1982, abandoned.

[51] Int. Cl.³ .............................................. A61M 1/00
[52] U.S. Cl. ..................................... 604/197; 604/263
[58] Field of Search ............... 604/192, 217, 263, 264, 604/265, 197

[56] References Cited

U.S. PATENT DOCUMENTS

| | | | |
|---|---|---|---|
| 3,225,763 | 12/1965 | Schaller | 604/192 |
| 3,303,847 | 4/1967 | Eaton | 128/232 |
| 3,507,280 | 4/1970 | Pollock | 128/232 |
| 3,559,645 | 2/1971 | Schaller | 604/192 |
| 3,802,434 | 4/1974 | Brooks | 128/232 |
| 3,905,370 | 9/1975 | Lazdowski | 128/232 |
| 3,968,797 | 7/1976 | Packer | 128/232 |
| 4,068,663 | 1/1978 | D'Alessandro | 128/232 |

FOREIGN PATENT DOCUMENTS 868134 5/1961 United Kingdom ............... 604/263

Primary Examiner—John D. Yasko
Attorney, Agent, or Firm—Frost & Jacobs

[57] ABSTRACT

A disposable plastic container-applicator usable as a douche having an integrally formed catheter and a container portion with a cover member enclosing the catheter. The cover member is sealed to the catheter both at a constricted portion and at a skirt portion to prevent the escape of fluid from the catheter into the surrounding atmosphere. A groove on the neck of the catheter engages a ridge on the skirt portion to form a seal. The inside diameter of the tip of the cover member is greater than the outside diameter of the catheter so as to form a cavity. To open a slit in the rounded end of the catheter for the passage of fluid, the user pinches the tip to cause the air of the cavity to pass through the slit.

15 Claims, 4 Drawing Figures

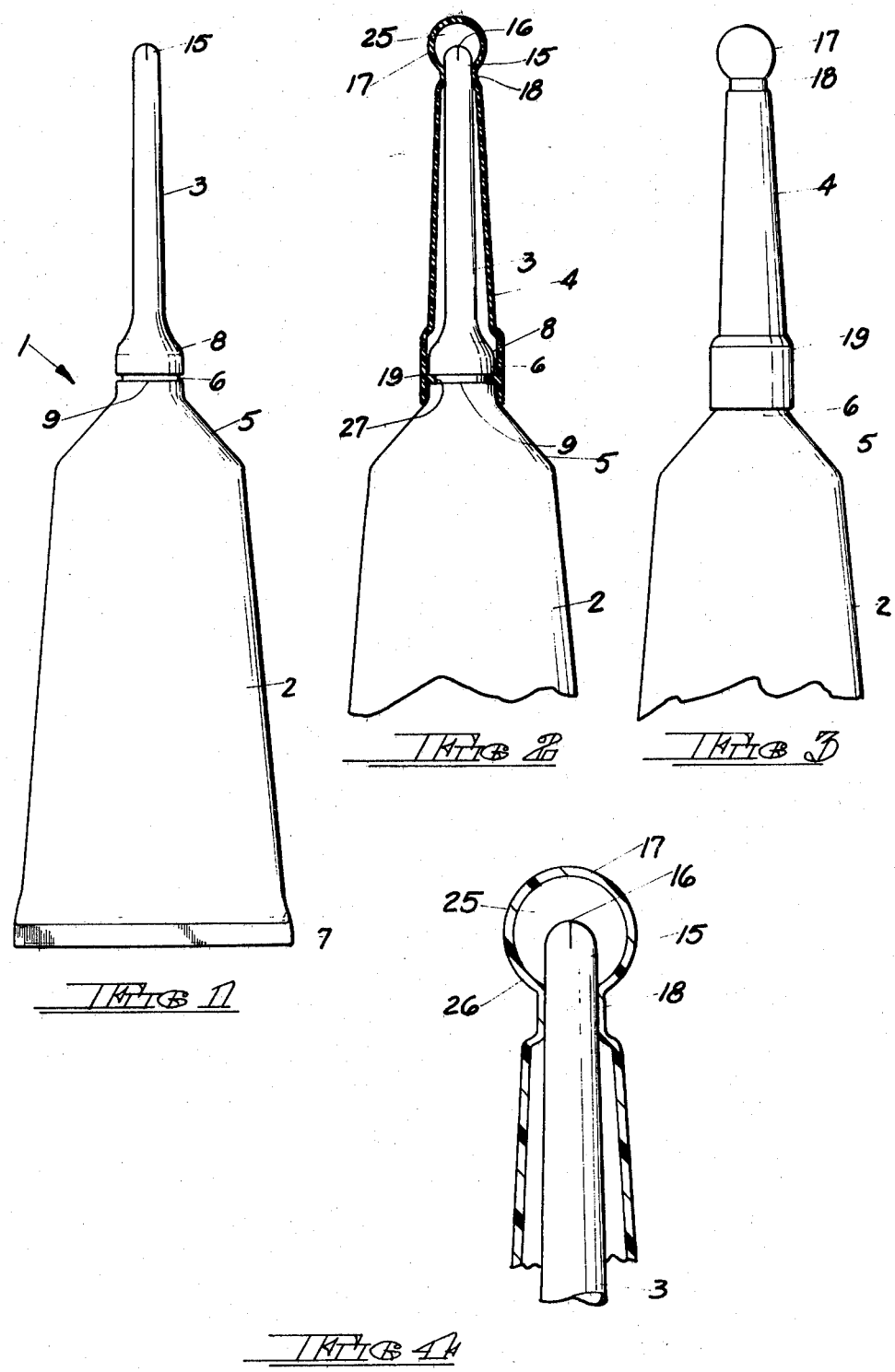

DISPOSABLE CONTAINER-APPLICATOR WITH LEAK-PROOF COVER

This application is a continuation of application Ser. No. 369,092, filed Apr. 16, 1982, now abandoned.

SUMMARY OF THE INVENTION

The present invention relates to a disposable container-applicator for dispensing liquids, creams and various fluids. More particularly, the invention relates to a plastic disposable container-applicator used as a douche having a cover member and a lubricant to prevent leakage of the contents prior to use.

For sanitary and practical reasons, it is desirable to have a container-applicator used as a douche which is formed of one integral piece of material and which is filled with the liquid contents at the time of manufacturing the container-applicator. The catheter of the container-applicator should have one or more perforations or slits through which the contents can be sufficiently dispensed by the user without the user needing to make additional apertures in the catheter. Additionally, a lubricant should be provided on the catheter to eliminate the necessity of the user separately purchasing and applying a lubricant to the catheter. Essentially, the modern user of the container-applicator as a douche desires a commercially available product which is ready to use.

The prior art, however, has failed to provide a prefilled integral container-applicator which does not readily dispel the contents prior to use when pressure is applied to the container. Frequently, in the transportation and storage of the douche container-applicator, sufficient weight is brought upon the container so that the fluid contents of the container-applicator are expelled through the catheter perforations. Such undesired evacuations of the container causes numerous handling and storage problems as well as resulting in the user purchasing a container-applicator which is not full of solution. Similarly, a user handling the container-applicator prior to application may inadvertently squeeze the container body so as to cause the fluid to flow from the container and thereby waste solution.

An example of a prior art douche which provides an integral one-piece container-applicator with a cover member is provided in U.S. Pat. No. 3,303,847 issued to Chester C. Eaton. However, the douche disclosed in that patent reference lacks the numerous sealing means of the present invention and hence, it is not as effective as the present invention in preventing undesired leakage.

Many prior art devices increase the risk of undesired preuse dispelment of the container fluid by requiring the user to squeeze the container body in order to open the apertures in the catheter to allow the fluid to flow. If the user is not careful, then this preuse pressure on the container will result in a needless waste of container fluid as well as causing the surrounding area to be sprayed with the fluid. The prior are requires the user to know the amount of pressure which is sufficient to open the catheter perforations but which is insufficient to cause the undesired spillage. Prior devices have failed to provide a means of activating the aperture in the catheter without requiring pressure to be applied to the fluid container itself.

The present invention obviates these disadvantages inherent in the prior art by furnishing a container-applicator usable as a douche which is both leak-proof and activated by means other than applying pressure directly to the fluid field container. This allows the container-applicator to be shipped and stored without fear of accidently dispelling fluid due to the placement of pressure on the container-applicator. Similarly, once the user has purchased the container-applicator, it can be easily stored and handled without the possibility of the contents being inadvertently discharged. The present invention provides a douche assembly which can be activated prior to use without the need of using the fluid within the container to open the catheter perforations. Essentially, the container-applicator of the present invention prevents undesired leakage of the fluid.

In a preferred embodiment, the disposable plastic container-applicator has a collapsible container portion, a flexible elongated tubular catheter, and a hollow, removable, flexible cover member enclosing the catheter. The end of the catheter has one or more perforations. The catheter is attached to the container portion for the passage of fluid from the container portion to the catheter and out the perforation when pressure is applied to the container portion by the user. The neck of the container portion has a groove circumscribing the neck. A ridge extends perpendicularly outward from the inside surface of the cover member near the open end of the cover member and the ridge engages the groove of the neck to seal the cover member to the neck. The tip of the cover member has an inside surface diameter greater than the outside diameter of the catheter. The catheter has a constricted portion at which the inside surface of the cover member frictionally engages the catheter. A cavity is formed between the inside surface of the cover member tip and the outside surface of the catheter. The cavity is sealed from the atmosphere by the constricted portion. The cavity allows for the opening of the perforation in the catheter by forcing the air out of the cavity through the perforation when pressure is applied to the tip by the user. Additionally, the cavity can contain a lubricant which both seals a slit in the end of the catheter and lubricates the catheter end.

While for purposes of the exemplary embodiment, the present invention is shown as a disposable container-applicator usable as a douche, it will be understood by one skilled in the art that the container-applicator may be used to contain and dispense various types of liquids, creams, medicinal or pharmaceutical preparations within human and animal orifices or within the small openings of various objects which require a long tubular applicator to gain access.

DESCRIPTION OF THE DRAWINGS

FIG. 1 is an elevational view of the container-applicator of the present invention.

FIG. 2 is a fragmentary cross-sectional view of the container-applicator showing the cover member enclosing the catheter.

FIG. 3 is a fragmentary view of the container-applicator showing the cover member enclosing the catheter.

FIG. 4 is a fragmentary cross-sectional view of the cavity formed between the cover member and the catheter tip of the container-applicator.

DESCRIPTION OF THE PREFERRED EMBODIMENT

Referring now to FIGS. 1 and 2, the container-applicator 1 includes a collapsible container portion 2, a flexible elongated tubular catheter 3, and a hollow, removable, flexible cover member 4. The container portion 2 and the container-applicator 3 are manufactured as one integral unit. The container portion 2 terminates in a hollow conical portion 5 upon which a hollow cylindrical neck 6 is surmounted. The catheter 3 joins the container portion 2 at the neck 6.

The container portion 2 is a flexible, hollow member formed from plastic with a filling end 7 for introducing the solutions into the container portion 2. The filling end 7 is open during manufacture and then fishtailed and sealed after the container portion 2 is filled with the desired fluid. Conventional filling and sealing means are used to effectuate this operation.

The neck 6 is of a greater diameter than that of the catheter 3 while the container portion 2 has a diameter greater than that of the neck 6. The neck 6 terminates in the catheter 3 where the shoulder 8 is formed at the juncture of the neck 6 and the catheter 3. A groove 9 circumscribes the neck 6.

The catheter 3 has a smooth uninterrupted surface terminating in a rounded end 15 which has one or more perforations for the passage of fluid. Preferably, the perforation is a slit 16 across the rounded end 15, dividing the rounded end 15 into approximately two equal portions. During use of the container-applicator 1, when the container portion 2 is squeezed, the fluid flows out of the container portion 2, through the conical portion 5 and the neck 6, into the catheter 3, and out of the slit 16.

A hollow, removable, flexible cover member 4 encloses the catheter 3 and a portion of the neck 6 to protect the catheter 3 during shipping and storage and to prevent undesired leakage of the fluid from the container portion 2. The cover member 4 has a tip 17, a constricted portion 18 and a thin flexible skirt 19 at the open end of the cover member 4.

As shown in FIG. 4, the tip 17 has an inside surface diameter greater than the outside surface diameter of the catheter 3 so as to form a cavity 25. Within the cavity 25, a lubricant, such as petroleum jelly, can be placed to coat and lubricate the rounded end 15 of the catheter 3. The lubricant also provides a sealing layer over the slit 16 to prevent the accidental discharge of fluid from the catheter 3. If desired, the lubricant may also be provided on the catheter 3 between the constricted portion 18 and the neck 6 so as to ease the usage of the container-applicator 1.

The tip 17 tapers to form a constricted portion 18 in the catheter 3. The inside surface of the constricted portion 18 has a diameter slightly less than the outside diameter of the catheter 3 and frictionally engages the catheter 3 to seal the cavity 25 from the atmosphere. A lubricant may be applied to a taper portion 26 which joins the tip 17 to the constricted portion 18 to further seal the cavity 25 from the atmosphere and to prevent leakage of fluid out of the cavity 25. Thus, even if fluid from the container portion 2 should inadvertently be dispelled through the slit 16, the tight fit of the constricted portion 18 to the catheter 3 will prevent the fluid in the cavity 25 from escaping and inconveniencing the user.

A thin flexible skirt 19, located at the open end of the cover member 4, fits onto the neck 6 of the catheter 3. To effectuate a tight fit between the skirt 19 and the neck 6, the inside diameter of the skirt 19 should be less than the outside diameter of the neck 6. A ridge 27 extends perpendicularly outward from the inside surface of the cover member 4 near the open end of the skirt portion 19. The ridge 27 is of a sufficient size to fit into the groove 9 on the neck 6 so as to secure the cover member 4 onto the neck 6 so that the catheter 3 is protected. By the interaction of the ridge 27 with the groove 9, the cover member 4 seals off the catheter 3 from the atmosphere. If fluid from the container portion 2 should escape pass the seal of the constricted portion 18 with the catheter 3, then the seal of the ridge 27 with the groove 9 at the skirt portion 19 will prevent the leakage of the fluid. Between the constricted portion 18 and the skirt portion 19, the cover member 4 has an inside diameter greater than the outside diameter of the catheter The container-applicator 1 may be made of any suitable, flexible materials, and plastic has been found to provide the requisite properties. The container-applicator 1 may be formed as one integral unit by various techniques, including blow molding and dip molding. The plastic selected for the container-applicator 1 should be nonreactive with the fluid contained therein and be medically safe for use in the desired application.

When manufactured, the container portion 2 and the catheter 3 are formed as one integral unit. The desired fluid is introduced into the container portion 2 through the filling end 7. After the container portion 2 is filled, the filling end 7 is sealed and the cover member 4 is locked onto the catheter 3 to prevent seapage of the fluid during the transportation and storage of the container-applicator 1. For the fluid from the container-applicator 1 to escape from the container portion 2 into the surrounding atmosphere, the fluid would have to break the seal of the lubricant over the slit 16, pass through the seal of the constricted portion 18 with the catheter 3, and finally seap through the seal at the skirt portion 19 of the groove 9 with the ridge 27. Only then, if all three seals fail, will the fluid come into the undesired contact with the user or be sprayed inadvertently into the surrounding atmosphere.

To use the container-applicator 1, the user pinches the tip 17 of the cover member 4. This pinching creates pressure in the cavity 27, which causes the slit 16 in the rounded end 15 to be opened. Since the cavity 25 is sealed from the atmosphere at the constricted portion 18, the air within the cavity 25 may only pass through the slit 16, thereby opening the slit 16 to allow for passage of the fluid within the container portion 2. After the slit 16 has been opened, the user removes the cover member 4 from the catheter 3 by disengaging the ridge 27 from the groove 9. This is best accomplished by first bending the pliable catheter 3 and cover member 4 at a 90° angle with respect to the neck 6 and then pulling the cover member 4 away from the neck 6. The bending of the catheter 3 and the cover member 4 aids the disengagement of the ridge 27 from the groove 9. When the cover member 4 has been removed from the catheter 3, the container-applicator 1 is ready to use since the lubricant has already been applied to the catheter 3 at the time of manufacture.

What is claimed is:

1. A disposable plastic container-applicator comprising:

(a) a collapsible container portion filled with a fluid;

(b) a flexible elongated tubular catheter having one or more perforations in the end of the catheter, the catheter attached to the container portion for the passage of fluid from the container portion to the catheter and out the perforations when pressure is applied to the container portion by a user;

(c) a hollow, completely removable, flexible cover member enclosing the catheter;

(d) a neck of the container portion having a groove circumscribing the neck;

(e) a ridge extending perpendicular with respect to the length of said catheter and perpendicularly outward from the inside surface of the cover member near the open end of the cover member and the ridge engaging the groove of the neck for sealing the cover member to the neck;

(f) a tip of the cover member having an inside surface diameter greater than the outside diameter of the catheter;

(g) a constricted portion of the cover member adjacent the tip at which the inside surface of the cover member frictionally engages the catheter; said constricted portion extending length-wise along the catheter a distance of approximately the diameter of the catheter adjacent the constructed portion;

(h) an intermediate portion of said cover member between said constricted portion and said ridge of said cover member in which the diameter of said intermediate portion is greater than the outside diameter of the catheter; and (i) the inside surface of the tip of said cover member and the outside diameter of the catheter forming a cavity between the catheter and the cover member, the cavity being sealed from the atmosphere by the constricted portion, the cavity allowing for the opening of the perforation in the catheter by forcing the air of the cavity through the perforation when pressure is applied to the tip by the user, the constricted portion preventing fluid from flowing out of the cavity prior to use of the container-applicator.

2. A disposable plastic container-applicator as described in claim 1, wherein one or more perforations in the tubular catheter is a slit at the end of the catheter.

3. A disposable plastic container-applicator as described in claim 1, wherein the cavity formed by the inside surface of the tip of the cover member and the outside diameter of the catheter contains a lubricant.

4. A disposable plastic container-applicator as described in claim 3, wherein the lubricant seals the slit in the end of the catheter and lubricates the end of the catheter.

5. A disposable plastic container-applicator as described in claim 3, wherein the lubricant is a petroleum jelly.

6. A disposable plastic container-applicator as described in claim 1, wherein a taper portion between the tip and the constricted portion of the cover member has a lubricant for sealing the cavity from the atmosphere.

7. A disposable plastic container-applicator as described in claim 1, wherein the catheter has a smooth, uninterrupted surface terminating in a rounded end.

8. A disposable plastic container-applicator as described in claim 1, wherein the container portion comprises a flexible, hollow member having an open end for filling purposes, the open end being capable of being fishtailed and sealed after the container portion is filled with a fluid.

9. A disposable plastic container-applicator as described in claim 1, wherein the inside surface of the constricted portion has a diameter less than the outside diameter of the catheter.

10. A disposable plastic container-applicator as described in claim 1, wherein the cover member has a thin flexible skirt at the open end of the cover member, the inside diameter of the skirt being slightly less than the outside diameter of the neck.

11. A disposable plastic container-applicator as described in claim 1, wherein the portion of the cover member between the constricted portion and the skirt has an inside diameter greater than the outside diameter of the catheter.

12. A disposable plastic container-applicator as described in claim 1, wherein a lubricant is placed on the catheter between the constricted portion and the neck.

13. A disposable plastic container-applicator as described in claim 1, wherein said cover member includes an expanded end portion, which is greater in diameter than said intermediate portion, and said ridge is located in said expanded end portion.

14. A disposable plastic container-applicator as described in 13, wherein said expanded end portion is greater in diameter than said tip of said cover member.

15. A disposable plastic container-applicator as described in 1, wherein said groove is perpendicular to the length of said catheter and said ridge is perpendicular to said expanded end portion.

* * * * *